United States Patent [19]

Kawamata et al.

[11] Patent Number: 4,778,823

[45] Date of Patent: Oct. 18, 1988

[54] AMIDE DERIVATIVE AND EXTERNAL MEDICAMENT COMPRISING SAME

[75] Inventors: Akira Kawamata, Utsunomiya; Shinji Yano, Ichikai; Michihiro Hattori, Utsunomiya; Shuichi Akazaki, Ichikai; Genji Imokawa; Naotake Takaishi, both of Utsunomiya, all of Japan

[73] Assignee: Kao Corporation, Tokyo, Japan

[21] Appl. No.: 938,954

[22] Filed: Dec. 8, 1986

[30] Foreign Application Priority Data

Dec. 20, 1985 [JP] Japan ............... 286999
Oct. 22, 1986 [JP] Japan ............... 251485

[51] Int. Cl.$^4$ ............ C09F 5/00; B01F 17/30; A61K 31/16
[52] U.S. Cl. ............... 514/625; 514/627; 260/404; 252/357
[58] Field of Search ............ 260/404; 514/625, 627; 252/357

[56] References Cited

U.S. PATENT DOCUMENTS

| | | | |
|---|---|---|---|
| 2,746,897 | 5/1956 | Roder et al. | 260/404 |
| 3,387,008 | 6/1968 | Cawley | 260/404 |
| 3,439,007 | 4/1969 | Milks | 260/404 |
| 3,515,754 | 6/1970 | Mod et al. | 260/404 |
| 3,519,661 | 7/1970 | Mod et al. | 260/404 |
| 3,637,495 | 1/1972 | Eckert et al. | 260/404 |
| 3,681,333 | 8/1972 | Litt et al. | 260/404 |
| 4,313,888 | 2/1982 | Honda et al. | 260/404 |

FOREIGN PATENT DOCUMENTS 688048  2/1953  United Kingdom ........ 260/404

*Primary Examiner*—Alan Siegel
*Attorney, Agent, or Firm*—Oblon, Fisher, Spivak, McClelland & Maier

[57] ABSTRACT

An external medicament comprises a novel amide derivative represented by the following formula (I).

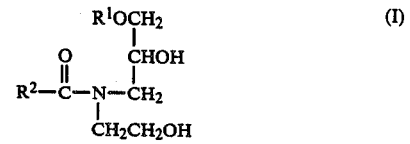

The external medicament is applicable to both a pharmaceutical external medicament and a cosmetic composition, and it provides excellent improving and preventing effects for chapping of the skin.

3 Claims, No Drawings

AMIDE DERIVATIVE AND EXTERNAL MEDICAMENT COMPRISING SAME

BACKGROUND OF THE INVENTION 1. Field of the Invention

This invention relates to an amide derivative and an external medicament comprising such derivative and, more particularly, to external medicament capable of enhancing the moisture retainability of keratin layers thereby improving chapping of the skin. 2. Description of the Prior Art It has hitherto been known that water content in keratin layers is an important factor for moistening and softening skin. It is considered that the water content is retained by water-soluble ingredients contained in the keratin layers, i.e., free amino acids, organic acids, urea or inorganic ions. These substances are incorporated solely or in combination into pharmaceutical external medicament or cosmetic composition in order to improve or prevent chapping of the skin.

Aside from the foregoings, many moisture retaining substances having high affinity with water have been developed and used for the same purpose.

However, these moisture retaining substances, when applied to the skin, remain on the keratin layers of the skin, serve to supply water thereto and act only temporarily thereby providing no fundamental improvement for the water retainability of the keratin layers or essential prevention or cure of chappings in the skin.

SUMMARY OF THE INVENTION

In view of the above situation, the present inventors have made an earnest study for overcoming the foregoing problems and have accomplished this invention based on the finding that the amide derivative synthesized for the first time by the present inventors and represented by the following general formula (I)

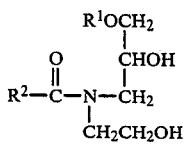
(I)

wherein $R^1$ represents a linear or branched, saturated or unsaturated hydrocarbon group having 10 to 26 carbon atoms, and $R^2$ represents a linear or branched, saturated or unsaturated hydrocarbon group having 9 to 25 carbon atoms, exhibits an effect of fundamentally improving the water retainability of keratin layers and that this effect can further be improved by the combined use of a surface active agent with the amide derivative.

That is, this invention provides an amide derivative represented by the formula (I) as described above and an external medicament comprising the amide derivative (I). This invention further provides an external medicament comprising the amide derivative (I) and a surface active agent.

DETAILED DESCRIPTION OF THE INVENTION AND PREFERRED EMBODIMENTS

The amide derivative represented by the formula (I) to be used in this invention can be prepared according to known methods (disclosed, for instance, in "Polish Journal of Chemistry" 52, 1059 (1978) and ibid. 52, 1983 (1978): Japanese Patent Application Laid-Open Nos. 117421/1979, 144308/1979 and 147937/1979). That is, it can be prepared by acylating a compound (II) obtained from glycidyl ether and ethanol amine and then selectively hydrolyzing the ester groups therein according to the reaction scheme shown below:

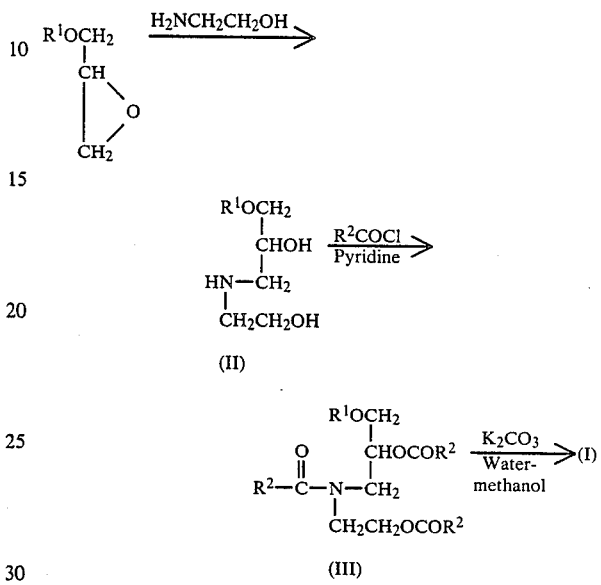

wherein $R^1$ and $R_2$ have the same meanings as described above.

The amide derivative represented by the formula (I) can also be prepared by reacting the compound (II) obtained above directly with a fatty acid methyl ester without isolation.

The amount of the amide derivative (I) to be incorporated into the external medicament according to this invention has no particular restriction but it is used in an amount from 0.001 to 50% by weight (hereinafter simply represented by %), preferably, from 0.1 to 20% in the case of usual emulsion type external medicament and, from 1 to 50% and, preferably, from 5 to 25% in the case of oily external medicament based on liquid hydrocarbon such as squalene.

As the surface active agent, any of nonionic surface active agents, anionic surface active agent and amphoteric surface active agents may be used. Of these, nonionic surface active agents are preferred.

Nonionic surface active agent can include, for instance, polyoxyethylene alkyl ether, polyoxyethylene alkylphenyl ether, polyoxyethylene fatty acid ester, sorbitan fatty acid ester, polyoxyethylene sorbitan fatty acid ester, fatty acid monoglyceride and glyceryl ether. Among them, preferred are those glyceryl ethers represented by the following general formula (IV):

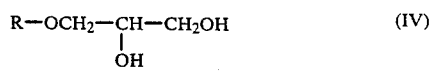
(IV)

wherein R represents an alkyl group of 8 to 24 carbon atoms and, particularly preferred are those compounds of the formula (IV) in which R is represented by the following formula (V):

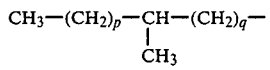

wherein p represents an integer from 4 to 10, q represents an integer from 5 to 11, p+q=11 to 17 and having a distribution peak at p=7 and q=8.

The incorporation amount of the surface active agent is from 0.01 to 20%, preferably from 0.1 to 5% based on the total composition.

The external medicaments of this invention are generally classified into a pharmaceutical external medicament and a cosmetic composition, according to their use.

As a pharmaceutical external medicament, for example, various kinds of ointments containing medicinal components can be listed. The ointment may be based on either of oily basic agents or oil-in-water or water-in-oil emulsiton type basic agents. The oily basic agents can include with no particular restriction, for example, vegetable oils, animal oils, synthetic oils, fatty acids, natural or synthetic glycerides. As the medicinal components, anodyne, antiphlogistic agents, itch-killers, sterilizing and disinfecting agents, astringent, skin softening agents, hormon preparations and the like can be incorporated as required with no particular restrictions.

In the application use as cosmetic composition, those generally employed as cosmetic ingredients such as oily components, moisture retaining agents, UV-ray absorbers, alcohols, chelating agents, pH adjusting agents, antiseptics, thickners, colorants and perfumes can optionally be combined and blended in addition to the essential ingredients.

The cosmetic compositions may be prepared in various forms of skin cosmetics such as water-in-oil or oil-in-water type emulsion cosmetics, creams, milky lotions, liquid face lotions, oily face lotions, lip sticks, foundations, skin cleaning agents, hair tonics, hair conditioners, hair nourishing agent or hair growers.

Although not completely known for the details of the operation mechanisms of the amide derivative represented by the general formula (I) in the external medicament according to this invention, it is presumed that the derivative re-constitutes lipid membrances between keratin cells, so that the keratin layers exhibit water retainability.

Since the external medicament according to this invention contains the amide derivative (I) having above property, it can provide excellent improving and preventing effects for chapping of the skin.

This invention will now be explained referring to examples.

EXAMPLE 1

Synthesis of
N-(2-hydroxy-3-hexadecyloxypropyl)-N-2-hydroxyethylhexadecanamide (Ia) [$R^1=C_{16}H_{33}$, $R^2=C_{15}H_{31}$ in the formula (I)]

(i) Synthesis of N-(2-hydroxy-3-hexadecyloxypropyl) ethanolamine (IIa):

In a 200 ml four-necked flask equipped with a stirrer, a dropping funnel, a thermometer and a reflux condenser, 61.1 g (1.0 mol) of ethanolamine was stirred under heating at 60°–70° C., and 24.3 g (0.082 mol) of hexadecyl glycidyl ether was added dropwise for 45 minutes. After the addition was completed, the reaction mixture was stirred for additional 2 hours under the same conditions, followed by evaporation of unreacted ethanolamine under a reduced pressure (79°–81° C./20 Torr). The residue was purified over silica gel flash column chromatography to give 18.4 g of the above-captioned compound (IIa) (yield 63%).

$^1$H-NMR $\delta$CDCl$_3$: 0.85(3H, t), 1.23(28H, br. s), 2.6–2.8(4H, m), 3.1–3.9(10H, m).

(ii) Synthesis of N-(2-hexadecanoyloxy-3-hexadecyloxypropyl)-N-2-hexadecanoyloxyethylhexadecanamide (IIIa):

15.2 g (0.042 mol) of the compound (IIa) obtained in (i) were dissolved in 200 ml of chloroform and 10.0 g (0.126 mol) of pyridine were added. Under water cooling, 34.6 g (0.126 mol) of hexadecanoyl chloride were added dropwise for 30 minutes and, after the addition was completed, the reaction mixture was stirred at room temperature for 2 hours. The reaction mixture was washed with water to remove pyridine hydrochloride and the solvent was distilled off to give 45.1 g of a crude product of the compound (IIIa).

$^1$H-NMR $\delta$CDCl$_3$: 0.86(12H, t), 1.25(106H, br. s), 2.2–2.4(6H, m), 3.3–3.6(8H, m), 4.0–4.3(2H, m), 5.1–5.2(1H, m).

(iii) Synthesis of the title compound (Ia):

5.8 g (0.084 ml) of potassium carbonate was added to the suspension of 45.1 g of the crude (IIIa) in 450 g of solvent mixture as water/methanol=1/1 and reaction mixture was refluxed for 3 hours. After reaction was completed, chloroform-soluble matters were extracted from the reaction mixture and purified over silica gel flash column chromatography to give 15.0 g of the title compound (Ia) as colorless powder (yield 60%, based on (IIa)). The compound (Ia) exhibited satisfactory physical and analytical data.

mp.: 74.9°–75.3° C.

IR $\nu$KBr(Cm$^{-1}$): 3320br, 2924, 2852, 1616, 1468, 1442, 1378, 1112, 1062, 722.

$^1$H-NMR $\delta$CDCl$_3$: 0.86(6H, t), 1.0–1.6(54H, m), 2.2–2.5(2H, m), 3.1–4.1(13H, m).

Elementary analysis: Calculated (%): C 74.31, H 12.64, N 2.34. Found (%): C 74.12, H 12.70, N 2.23.

EXAMPLE 2

Synthesis of
N-(2-hydroxy-3-hexadecyloxypropyl)-N-2-hydroxyethylhexadecanamide (Ia) [$R^1=C_{16}H_{33}$, $R^2=C_{15}H_{31}$ in the formula (I)]

In a 5 liter four-necked flask equipped with a stirrer, a dropping funnel, a thermometer, a reflux condenser and a gas inlet tube, 1637 g (26.8 mol) of ethanolamine and 327 g (7.11 mol) of ethanol were stirred at 80° C. in N$_2$ atmosphere. To the solution, 400 g (1.34 mol) of hexadecyl glycidyl ether were added dropwise for three hours. After the addition was completed, the reaction mixture was stirred under the same conditions for additional 30 minutes and then ethanol and unreacted etahanolamine were removed in vacuum (79°–81° C./20 Torr). 3.76 g (0.067 mol) of potassium hydroxide were added to the residue and, was stirred at 80° C./20 Torr. To the solution, 362.3 g (1.34 mol) of methylhexadecanoate were added dropwise for 3 hours. After the addition was completed, the reaction mixture was stirred for additional one hour under the same conditions to give 801 g of pale yellow crude product. The product was recrystallized once from hexane and following twice from ethanol to give 649 g of the title compound (Ia) as colorless powder (yield 81%).

mp.: 74°–76° C.

IR (cm$^{-1}$): 3320(br), 2924, 2852, 1616, 1468, 1112, 1062.

$^1$H-NMR: 0.86(6H, t), 1.0–1.6(54H, m), 2.2–2.5(2H, m), 3.2–4.1(13H, m)

Elementary analysis: Calculated (%): C 74.31, H 12.64, N 2.34. Found (%): C 74.12, H 12.70, N 2.23.

EXAMPLE 3

Synthesis of N-(2-hydroxy-3-decyloxypropyl)-N-2-hydroxyethyl-decanamide (Ib) [$R^1 = C_{10}H_{21}$, $R^2 = C_9H_{19}$ in the formula (I)]

The title compound as colorless powder (Ib) was obtained in the same procedure as in Example 2 by using decyl glycidyl ether and methyl decanoate (yield 71%).

mp.: 46°–49° C.

IR (cm$^{-1}$): 3316(br.), 2920, 2860, 1620, 1470, 1107, 1085.

$^1$H-NMR: 0.86(6H, t), 1.0–1.6(30H, m), 2.2–2.5(2H, m), 3.1–4.1(13H, m).

Elemantary analysis: Calculated (%): C 69.88, H 11.96, N 3.26. Found (%): C 70.25, H 11.95, N 3.16.

EXAMPLE 4

Synthesis of N-(2-hydroxy-3-decyloxypropyl)-N-2-hydroxyethyl-docosanamide (Ic) [$R^1 = C_{10}H_{21}$, $R^2 = C_{21}H_{43}$ in the formula (I)]

The title compound as colorless powder (Ic) was obtained in the same procedure as in Example 2 by using decyl glycidyl ether and methyl docosanoate (yield 80%).

mp.: 65°–68° C.

IR (cm$^{-1}$): 3310(br.), 2920, 2854, 1617.

$^1$H-NMR: 0.87(6H, t), 1.1–1.7(54H, m), 2.1–2.6(2H, m), 3.2–4.2(13H, m).

Elementary analysis: Calculated (%): C 74.31, H 12.64, N 2.34. Found (%): C 74.33, H 12.65, N 2.35.

EXAMPLE 5

Synthesis of N-(2-hydroxy-3-octadecyloxypropyl)-N-2-hydroxyethyldecanamide (Id) [$R^1 = C_{18}H_{37}$, $R^2 = C_9H_{19}$ in the formula (I)]

The title compound as colorless powder (Id) was obtained in the same procedure as in Example 2 by using octadecyl glycidyl ether and methyl decanoate (yield 78%).

mp.: 59°–61° C.

IR (cm$^{-1}$): 3298(br.), 2926, 2854, 1617, 1470, 1104, 1062.

$^1$H-NMR: 0.86(6H, t), 1.0–1.7(46H, m), 2.2–2.5(2H, m), 3.2–4.1(13H, m).

Elementary analysis: Calculated (%): C 73.14, H 12.46, N 2.58. Found (%): C 73.31, H 12.49, N 2.54.

EXAMPLE 6

Synthesis of N-(2-hydroxy-3-tetradecyloxypropyl)-N-2-hydroxyethyloleinamide (Ie) [$R^1 = C_{14}H_{29}$, $R^2 = $ cis-9-$C_{17}H_{33}$ in the formula (I)]

The title compound as colorless paste (Ie) was obtained in the same procedure as in Example 2 by using tetradecyl glycidyl ether and methyl oleate and purifying over silica gel chromatography (yield 85%).

mp.: 35°–40° C.

IR (cm$^{-1}$): 3400(br.), 2926, 2854, 1626, 1470, 1110, 1080.

$^1$H-NMR: 0.87(6H, t), 1.1–1.7(46H, m), 1.8–2.2(4H, m), 2.2–2.5(2H, m), 3.3–4.2(13H, m), 5.2–5.5(2H, m).

Elementary analysis: Calculated (%): C 74.57, H 12.35, N 2.35. Found (%): C 74.69, H 12.34, N 2.32.

EXAMPLE 7

Synthesis of N-(2-hydroxy-3-methylbranched octadecyloxypropyl)-N-2-hydroxyethyl-methyl-branched octadecanamide (If) [in the formula (I),

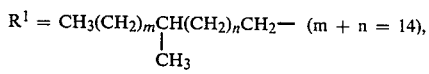

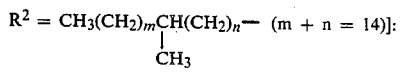

The title compound as colorless liquid (If) was obtained in the same procedure as in Example 6 by using methyl-branched octadecyl glycidyl ether and methyl-branched methyl octadecanoate (yield 84%).

mp.: 17°–30° C.

IR (cm$^{-1}$): 3400(br.), 2926, 2854, 1626, 1470, 1122.

$^1$H-NHR: 0.86(12H, t), 1.0–1.7(56H, m), 2.2–2.5(2H, m), 3.2–4.2(13H, m).

Elementary analysis: Calculated (%): C 75.28, H 12.79, N 2.14. Found (%): C 75.22, H 12.71, N 2.19.

EXAMPLE 8

By using a mixture of vaseline/compounds (Ia–f) = 3/1 (weight ratio) (product 1 according to this invention) and vaseline, skin conductance and chapping in the skin were evaluated by the following methods. The results are shown in Table 1.

Test Method

Different external medicaments were applied for two weeks on right and left cheeks of each of 10 female test panelers of 20–50 years old suffering from skin chapping in their cheeks in winter season. The test was conducted for the following items on the next day after completing the application for the two weeks.

(1) Skin conductance

After washing paneler's faces with warm water at 37° C. and keeping them quiet for 20 minutes in a room at a temperature of 20° C. and a humidity of 40%, the water content in the keratin layers was measured by a skin conductance meter (manufactured by IBS Co.). Lower conductance value means the severer skin chapping and the value less than 5 indicates remarkably severe skin chapping. On the other hand, if the conductance value is higher than 20, no substantial skin chapping was recognized.

(2) Score for skin chapping

Skin chapping was observed by naked eyes and judged by the following criterion. The score was indicated by an average value ± standard deviation.

| Score | Judgement for chapping |
|---|---|
| 0 | no chapping recognized |
| 1 | slight chapping recognized |
| 2 | chapping recognized |
| 3 | somewhat severe chapping recognized |

-continued

| Score | Judgement for chapping |
|---|---|
| 4 | severe chapping recognized |

TABLE 1

| | Skin Conductance | Chapping Score |
|---|---|---|
| Inventive Product 1 (Ia) | 20 ± 4.0 | 1.0 ± 0.2 |
| Inventive Product 1 (Ib) | 13 ± 1.2 | 1.3 ± 0.6 |
| Inventive Product 1 (Ic) | 19 ± 3.5 | 1.1 ± 0.3 |
| Inventive Product 1 (Id) | 18 ± 2.4 | 1.2 ± 0.3 |
| Inventive Product 1 (Ie) | 26 ± 4.0 | 0.8 ± 0.2 |
| Inventive Product 1 (If) | 23 ± 3.6 | 0.9 ± 0.2 |
| Vaseline | 6 ± 0.9 | 2.8 ± 0.7 |

EXAMPLE 9

By using the compounds (Ia–f) of this invention obtained in Example 1, the external medicaments (emulsion cosmetic compositions) having the formations shown in Table 2 were prepared and their effect for improving the skin chapping was evaluated by the same method as in Example 8. The results are shown in Table 3.

TABLE 2

| | Emulsion Cosmetic Composition (wt %) | | | | | |
|---|---|---|---|---|---|---|
| | Inventive Product | | | Comparative Product | | |
| Composition | 2 | 3 | 4 | 2 | 3 | 4 |
| Glyceryl ether [R in the formula (IV) is represented by the formula (V)] | 2.0 | — | — | 2.0 | — | — |
| Alginine monocetyl phosphate | — | 2.0 | — | — | 2.0 | — |
| Polyoxyethylene (20) sorbitan stearate | — | — | 1.0 | — | — | 1.0 |
| Sorbitan monostearate | — | — | 1.0 | — | — | 1.0 |
| 2-octyldodecyl-myristate | 10.0 | 10.0 | 10.0 | 10.0 | 10.0 | 10.0 |
| Vaseline | 3.0 | 3.0 | 3.0 | 3.0 | 3.0 | 3.0 |
| Squalane | 5.0 | 5.0 | 5.0 | 5.0 | 5.0 | 5.0 |
| Acetic acid tocophenol | 0.5 | 0.5 | 0.5 | 0.5 | 0.5 | 0.5 |
| Compound of the Invention (Ia–f) | 1.0 | 1.0 | 1.0 | — | — | — |
| Water | balance | → | → | → | → | → |

TABLE 3

| | Score for Skin Chapping | | |
|---|---|---|---|
| | 2 | 3 | 4 |
| Inventive Product (Ia) | 0.2 ± 0.2 | 0.4 ± 0.3 | 0.8 ± 0.3 |

TABLE 3-continued

| | Score for Skin Chapping | | |
|---|---|---|---|
| | 2 | 3 | 4 |
| Inventive Product (Ib) | 0.5 ± 0.3 | 0.7 ± 0.5 | 1.2 ± 0.5 |
| Inventive Product (Ic) | 0.2 ± 0.2 | 0.5 ± 0.3 | 0.8 ± 0.4 |
| Inventive Product (Id) | 0.3 ± 0.2 | 0.5 ± 0.4 | 0.8 ± 0.4 |
| Inventive Product (Ie) | 0.1 ± 0.1 | 0.3 ± 0.2 | 0.5 ± 0.2 |
| Inventive Product (If) | 0.1 ± 0.1 | 0.3 ± 0.2 | 0.7 ± 0.3 |
| Comparative Product | 2.1 ± 0.5 | 2.5 ± 0.5 | 2.6 ± 0.8 |

Note
Ten subjects

What is claimed is:

1. An amide derivative represented by the general formula (I):

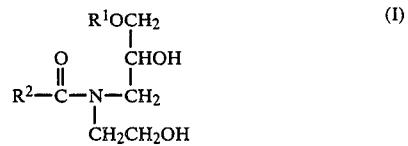

wherein $R^1$ represents a linear or branched, saturated or unsaturated hydrocarbon group having 10 to 26 carbon atoms and $R^2$ represents a linear or branched, saturated or unsaturated hydrocarbon group having 9 to 25 carbon atoms.

2. An external medicament comprising an amide derivative represented by the general formula (I):

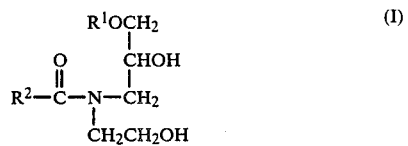

wherein $R^1$ represents a linear or branched, saturated or unsaturated hydrocarbon group having 10 to 26 carbon atoms and $R^2$ represents a linear or branched, saturated or unsaturated hydrocarbon group having 9 to 25 carbon atoms.

3. An external medicament comprising an amide derivative represented by the general formula (I)

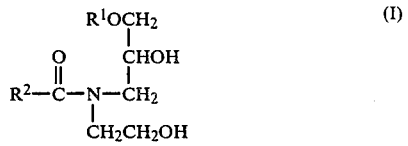

wherein $R^1$ represents a linear or branched, saturated or unsaturated hydrocarbon group having 10 to 26 carbon atoms and $R^2$ represents a linear or branched, saturated or unsaturated hydrocarbon group having 9 to 25 carbon atoms, and a surface active agent.

* * * * *